(12) United States Patent
Letendre et al.

(10) Patent No.: US 7,759,497 B2
(45) Date of Patent: *Jul. 20, 2010

(54) SYNTHESIS OF DIARYL PYRAZOLES

(75) Inventors: Leo J. Letendre, Manchester, MO (US);
William D. McGhee, Fenton, MO (US);
Cynthia Snoddy, St. Louis, MO (US);
George Klemm, Webster Groves, MO (US); Henry T. Gaud, Evanston, IL (US)

(73) Assignee: Pfizer Inc., New York, NY (US)

( * ) Notice: Subject to any disclaimer, the term of this patent is extended or adjusted under 35 U.S.C. 154(b) by 898 days.

This patent is subject to a terminal disclaimer.

(21) Appl. No.: 11/470,689

(22) Filed: Sep. 7, 2006

(65) Prior Publication Data

US 2007/0004924 A1 Jan. 4, 2007

Related U.S. Application Data

(63) Continuation of application No. 10/444,876, filed on May 23, 2003, now Pat. No. 7,141,678.

(60) Provisional application No. 60/383,007, filed on May 24, 2002.

(51) Int. Cl.
*C07D 231/12* (2006.01)
(52) U.S. Cl. .................................................. 548/377.1
(58) Field of Classification Search ............... 548/377.1
See application file for complete search history.

(56) References Cited

U.S. PATENT DOCUMENTS 5,521,207 A * 5/1996 Graneto ...................... 514/406
5,892,053 A * 4/1999 Zhi et al. .................. 548/377.1
5,910,597 A 6/1999 Zhi et al. .................. 548/377.1
6,150,534 A 11/2000 O'Shea et al. ........... 548/377.1
6,232,472 B1 5/2001 O'Shea et al. ........... 548/377.1
6,506,779 B1 * 1/2003 Cheng et al. ................. 514/341
7,141,678 B2 * 11/2006 Letendre et al. .......... 548/377.1

FOREIGN PATENT DOCUMENTS

| EP | 0418845 | 3/1991 |
| EP | 0554829 | 8/1993 |
| WO | WO 0042021 | 7/2000 |

OTHER PUBLICATIONS

Nishiwaki, Tarozaemon, *Studies on Heterocyclic Chemistry. IV.* Preparation of Several Trifluoromethyl-substituted Heterocyclic Compounds and Observation of Metastable Ion in the Mass Spectra of Trifluoromethyl-pyrazones, Bulletin of the Chemical Society of Japan, vol. 42, No. 10, pp. 3024-3026 (1969).
Soliman, et al., "Preparation and Antidiabetic Activity of New 3-Methyl-5-phenylpyrazolesulfonylurea Derivatives", *Journal of Pharmaceutical Sciences*, vol. 70(6), pp. 602-605 (1981).
Wright, et al., "The Antidiabetic Activity of 3,5-Dimethylpyrazoles", *Journal of Medicinal Chemistry*, vol. 7, pp. 102-105 (1964).
International Search Report, dated Jul. 30, 2003, for Application No. PCT/US03/16404.

* cited by examiner

*Primary Examiner*—Laura L. Stockton
(74) *Attorney, Agent, or Firm*—Jennifer Kispert; A. Dean Olson

(57) ABSTRACT

A process for the qualitative preparation of 3-haloalkyl-1H-pyrazoles suitable for efficient, high payload commercial application.

4 Claims, No Drawings

SYNTHESIS OF DIARYL PYRAZOLES

This application is a continuation of Application Ser. No. 10/444,876, filed May 23, 2003 now U.S. Pat. No. 7,141,678, which claims the benefit of U.S. Provisional Application Ser. No. 60/383,007, filed May 24, 2002, the entire disclosure of which is herein incorporated by reference.

BACKGROUND OF THE INVENTION

The present invention generally relates to the preparation of pyrazoles. In one embodiment, the present invention relates to a process for the formation of a 1-(4-sulfonylphenyl)pyrazole from the condensation of diketones and hydrazines.

Pyrazoles have been widely described as pharmaceutical therapeutic agents, including anti-inflammatories and antidiabetics. In particular, [3-haloalkyl-1H-pyrazole-1-yl] benzenesulfonamides have been used as potent antiinflammatories without the side effects commonly associated with previous anti-inflammatory agents.

The preparation of pyrazoles from the condensation of diketones and hydrazines has previously been reported. See, for example, European Patent No. 418,845, European Patent No. 554,829, T. Nishiwaki, *Bull. Chem. Soc. Japan,* 42, 3024-26 (1969); J. Wright et al., *J. Med. Chem.,* 7, 102-5 (1963); and R. Soliman and H. Feid-Allah, *J. Pharm. Sci.,* 70, 602-5 (1980). These methods, however, have been criticized as not providing a scalable commercial process.

In WO 00/42021, O'Shea et al. describe a two step process for the preparation of pyrazoles from the condensation, in an amide solvent, of a diketone and a hydrazine. The pyrazole is produced as a solvate of the amide solvent and is then isolated and recrystallized from isopropanol and water to produce an unsolvated pyrazole. Disadvantageously, however, the diketone is isolated prior to the condensation reaction with hydrazine, a multi-solvent system is used, more than one crystallization is required, and the payload is relatively low.

In U.S. Pat. Nos. 5,892,053 and 5,910,597, Zhi et al. describe a scalable two step process for the preparation of pyrazoles from the condensation of diketones and hydrazines. In the first step, a diketone is formed by the treatment of a ketone with base and ester in a suitable solvent. In the second step, the diketone is solubilized in an aqueous alcohol and condensed with a hydrazine to form the pyrazole product. This two step process has been used on a commercial scale for the preparation of celecoxib (4-[5-(4-methylphenyl)-3-(trifluoromethyl)-1H-pyrazole-1-yl]benzenesulfonamide) sold under the trademark CELEBREX® by Pharmacia Corporation as shown in the following reaction:

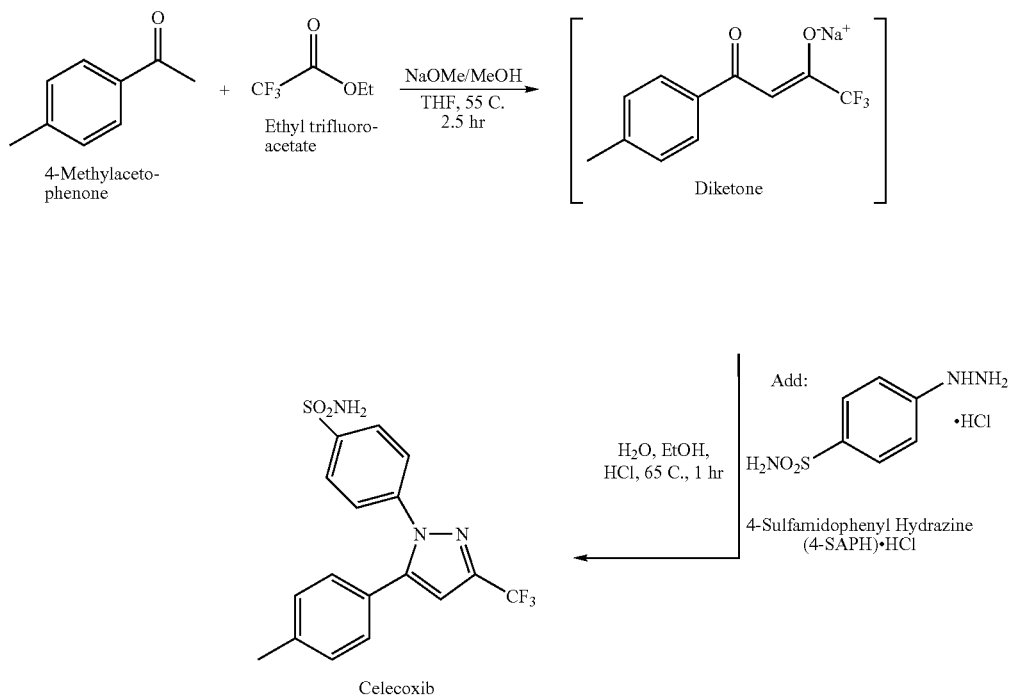

While this synthetic approach proceeds with high selectivity to celecoxib, about 2-5 wt. % of regioisomer and hydroxyregioisomer by-products are formed under commercial conditions.

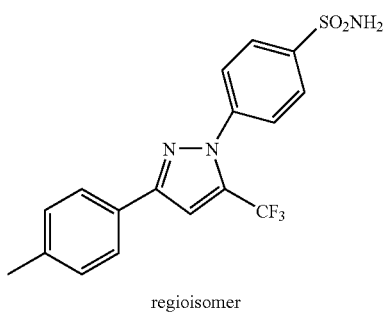

regioisomer

-continued

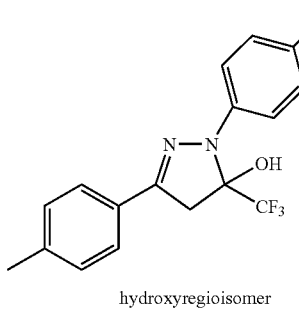

hydroxyregioisomer

The regioisomer and hydroxyregioisomer by-products must be separated from celecoxib in a purification step to enable the celecoxib to meet purity requirements. The separation is typically done through a crystallization step in which celecoxib preferentially crystallizes while the regioisomer and hydroxyregioisomer by-products predominantly remain in solution. The celecoxib crystals are then removed from the resultant slurry and separated from impurities by solid-liquid separation techniques known to those skilled in the art, such as centrifugation or filtration.

Under commercial conditions used to date, of the two by-products, regioisomer is selectively formed over hydroxyregioisomer. This is problematic, however, since the regioisomer is generally more difficult to separate through crystallization from celecoxib than is the hydroxyregioisomer, and regioisomer concentrations of greater than about 1% typically require two crystallizations to achieve desired celecoxib purity. The second crystallization adds time to the manufacturing process and thus negatively impacts product throughput. Additionally, a second crystallization reduces yield as some celecoxib remains uncrystallized and is not recovered from the liquid phase.

SUMMARY OF THE INVENTION

Among the various aspects of the present invention, therefore, is the provision of a process for the preparation of 3-haloalkyl-1H-pyrazoles, in general, and celecoxib, in particular. Advantageously, the regioisomer and hydroxyregioisomer are formed in relatively low concentrations and hydroxyregioisomer is preferentially formed over regioisomer. In addition, celecoxib may be isolated in relatively high purity and yield in a single direct crystallization from the reaction product mixture in a process that can be performed with increased payload.

Briefly, therefore, the present invention is directed to a process for the preparation of a crystallized reaction product constituting at least about 98% by weight of a 1-(4-sulfonylphenyl)pyrazole or a salt thereof by combining a source of a 1,3-diketone or a salt thereof with a source of 4-sulfonylphenylhydrazine or a salt thereof in a reaction mixture comprising a solvent system. The water content of the 1,3-diketone source is less than about 30 equivalents of water per equivalent of 1,3-diketone. The 1,3-diketone has the formula:

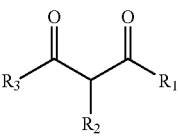

the 4-sulfonylphenylhydrazine has the formula:

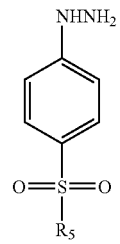

and the 1-(4-sulfonylphenyl)pyrazole has the formula:

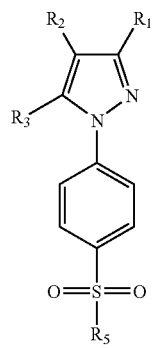

wherein $R_1$ is an ester or a hydrocarbyl substituted with one or more halogens;

$R_2$ is hydrogen, alkyl, cyano, hydroxyalkyl, cycloalkyl or alkylsulfonyl;

$R_3$ is phenyl substituted with one or more of an alkyl, a halogen, an ether, an acid or an acid ester; and $R_5$ is methyl, amino or substituted amino.

The present invention is also directed to a process for the preparation of a crystallized reaction product constituting at least about 98% by weight of a 1-(4-sulfonylphenyl)pyrazole or a salt thereof in which a source of a 1,3-diketone or a salt thereof is combined with a source of a salt of 4-sulfonylphenylhydrazine in a reaction mixture comprising a solvent system containing an organic solvent, and where the salt of 4-sulfonylphenylhydrazine has a solubility in the organic solvent of at least 0.05 molar. The 1,3-diketone has the formula:

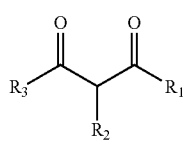

the 4-sulfonylphenylhydrazine has the formula:

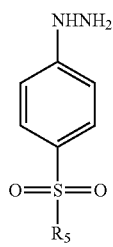

and the 1-(4-sulfonylphenyl)pyrazole has the formula:

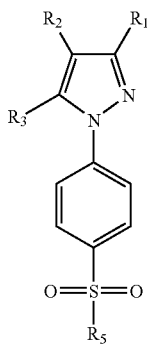

wherein $R_1$ is an ester or a hydrocarbyl substituted with one or more halogens;

$R_2$ is hydrogen, alkyl, cyano, hydroxyalkyl, cycloalkyl or alkylsulfonyl;

$R_3$ is phenyl substituted with one or more of an alkyl, a halogen, an ether, an acid or an acid ester; and $R_5$ is methyl, amino or substituted amino.

The present invention is also directed to a process for the preparation of celecoxib (4-[5-(4-methylphenyl)-3-(trifluoromethyl)-1H-pyrazole-1-yl]benzenesulfonamide) or the 4-fluorophenyl analog of celecoxib (4-[5-(4-fluorophenyl)-3-(trifluoromethyl)-1H-pyrazole-1-yl]benzenesulfonamide). In this process, a 1,3-diketone source containing a metal salt of 4-methylphenyl-1,1,1-trifluoro-2,4-butanedione or a metal salt of 4-fluorophenyl-1,1,1-trifluoro-2,4-butanedione and a base is combined with a source of a 4-sulfamidophenyl hydrazine halide salt additionally comprising an acid selected from the group consisting of trifluoroacetic, hexafluorophosphoric, tetrafluoroboric, trichloroacetic, difluoroacetic, and dichloroacetic in a reaction system containing an alcohol having at least 3 carbon atoms. The 1,3-diketone source and 4-sulfamidophenyl hydrazine halide salt thereby react to form celecoxib or the 4-fluorophenyl analog of celecoxib.

Other aspects and objects will be in part apparent and in part pointed out hereinafter.

DETAILED DESCRIPTION OF THE PREFERRED EMBODIMENTS

The present invention relates to an improved process for the preparation of 3-haloalkyl-1H-pyrazoles. More specifically, it has been discovered that 3-haloalkyl-1H-pyrazoles can be produced in high purity, with high relative payload and throughput, and in a single crystallization step from an essentially anhydrous single solvent system. This process may be used, for example, to increase 3-haloalkyl-1H-pyrazole yield by up to about 25%, increase batch size by up to about 75%, and reduce cycle time by up to about 65% over certain prior art processes. In addition, this process allows for the preparation of celecoxib and its 4-fluorophenyl analog which contain less than about 2%, more preferably less than about 1% and most preferably less than about 0.5% by-product.

In general, the process of the present invention allows for concentrated reactions thereby enabling high payload operations and increased throughput in existing manufacturing equipment resulting in significant commercial advantages. High payload operations are especially advantageous because less solvent is used per unit of product produced accruing the dual benefits of manufacturing cost and environmental burden reductions. Additional environmental and safety advantages may be realized because the solvent system comprises alcoholic solvents thereby eliminating the need for solvents such as amides, tetrahydrofuran (THF) and methyl tert-butyl ether (MTBE) which may raise potential safety and environmental concerns.

The process of the present invention may advantageously be used for the preparation of 3-haloalkyl-1H-pyrazoles, in general, and to the preparation of anti-inflammatory compounds of Formula (1), in particular:

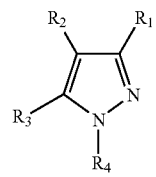

(1)

wherein $R_1$ is a substituted or unsubstituted hydrocarbyl and is electronegative relative to $R_3$;

$R_2$ is hydrogen, alkyl, cyano, hydroxyalkyl, cycloalkyl, alkylsulfonyl or halo;

$R_3$ is a substituted or unsubstituted hydrocarbyl and is electropositive relative to $R_1$; and $R_4$ is aryl substituted at a substitutable position with a substituted sulfonyl.

In one embodiment, $R_1$, is alkoxycarbonyl, haloalkyl, or substituted aryl, typically lower haloalkyl, $R_2$ is hydrogen, lower alkyl, cyano, lower hydroxyalkyl, lower cycloalkyl, lower alkylsulfonyl or halo, and $R_4$ is phenyl, substituted at a substitutable position with a substituted sulfonyl. In this embodiment, $R_3$ is substituted or unsubstituted cycloalkyl, cycloalkenyl, aryl or heteroaryl wherein the substituents of the cycloalkyl, cycloalkenyl, aryl or heteroaryl moieties are selected from halo, alkylthio, alkylsulfonyl, cyano, nitro, haloalkyl, alkyl, hydroxyl, alkenyl, hydroxyalkyl, carboxyl, cycloalkyl, alkylamino, dialkylamino, alkoxycarbonyl, aminocarbonyl, alkoxy, haloalkoxy, aminosulfonyl, heterocyclo and amino. In this embodiment, $R_3$ will typically be selected from lower cycloalkyl, lower cycloalkenyl, aryl, 5- or 6-membered heteroaryl, and lower heteroaryl, wherein $R_3$ is optionally substituted at a substitutable position with one or more radicals selected from halo, cyano, nitro, hydroxyl, carboxyl, cycloalkyl, aminocarbonyl, lower alkylthio, lower alkyl, lower alkenyl, lower alkoxycarbonyl, lower haloalkyl, lower alkoxy, lower hydroxyalkyl, lower haloalkoxy, lower N-alkylamino, lower N,N-dialkylamino, 5- or 6-membered heterocyclo and amino.

In another embodiment, $R_1$ is fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, or dichloropropyl, $R_2$ is hydrogen, methyl, ethyl, isopropyl, tert-butyl, isobutyl, hexyl, cyano, fluoro, chloro, bromo, methylsulfonyl, ethylsulfonyl, cyclopropyl, cyclopentyl, cyclobutyl, hydroxypropyl, or hydroxymethyl, and $R_4$ is phenyl-4-aminosulfonyl or phenyl-4-methylsulfonyl. In this embodiment, $R_3$ is phenyl, napthyl, biphenyl, cyclohexyl, cyclopentyl, cycloheptyl, 1-cyclohexenyl, 2-cyclohexenyl, 3-cyclohexenyl, 4-cyclohexenyl, 1-cyclopentenyl, 4-cyclopentenyl, benzofuryl, 2,3-dihydrobenzofuryl, 1,2,3,4-tetrahydronaphthyl, benzothienyl, idenyl, indanyl, indolyl, dihydroindolyl, chromanyl, benzopyran, thiochromanyl, benzothiopyran, benzodioxolyl, benzodioxanyl, pyridyl, thienyl, thiazolyl, oxazolyl, furyl or pyrazinyl, wherein $R_3$ is optionally substituted at a substitutable position with one or more radicals selected from fluoro, chloro, bromo, methylthio, methyl, ethyl, propyl, isopropyl, tert-butyl, isobutyl, hexyl, ethenyl, propenyl, methylsulfonyl, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, aminocarbonyl, fluoromethyl, difluoromethyl, trifluoromethyl, chloromethyl, dichloromethyl, trichloromethyl, pentafluoroethyl, heptafluoropropyl, bromodifluoromethyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, aminosulfonyl, hydroxypropyl, hydroxyisopropyl, hydroxymethyl, hydroxyethyl, trifluoromethoxy, amino, N-methylamino, N-ethylamino, N-ethyl-N-methylamino, N,N-dimethylamino, N,N-diethylamino, piperidinyl, piperazinyl, morpholino, cyclohexyl, cyclopropyl, cyclobutyl, or nitro.

Generally, pyrazole (1) is prepared by a condensation reaction of a diketone (2) and a hydrazine (3) in a suitable solvent as depicted in Reaction Scheme (I) below.

Reaction Scheme (I):

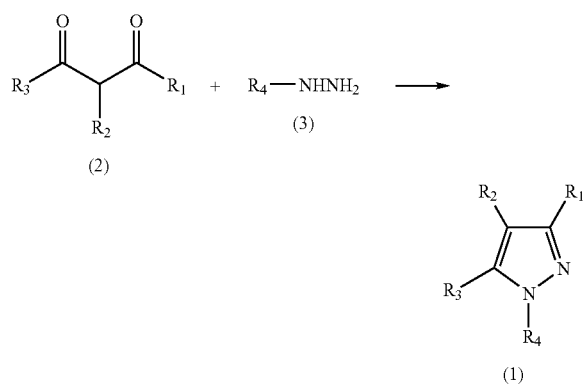

wherein $R_1$, $R_2$, $R_3$, and $R_4$ are as previously defined. Pyrazole (1) may be formed in a reaction mixture formed by combining a source of diketone (2) and a source of hydrazine (3) in a solvent system, for example, at a temperature of about 22° C. to about 70° C. The solvent system may comprise any organic solvent or mixture of solvents which is/are inert under the reaction conditions; in addition, the solvent system may be provided separately or as part of the diketone source or hydrazine source.

In one embodiment, diketone (4) and hydrazine (5) are condensed in an alcoholic solvent in the presence of an acid to form pyrazole (6) as depicted in Reaction Scheme (II) below.

Reaction Scheme (II):

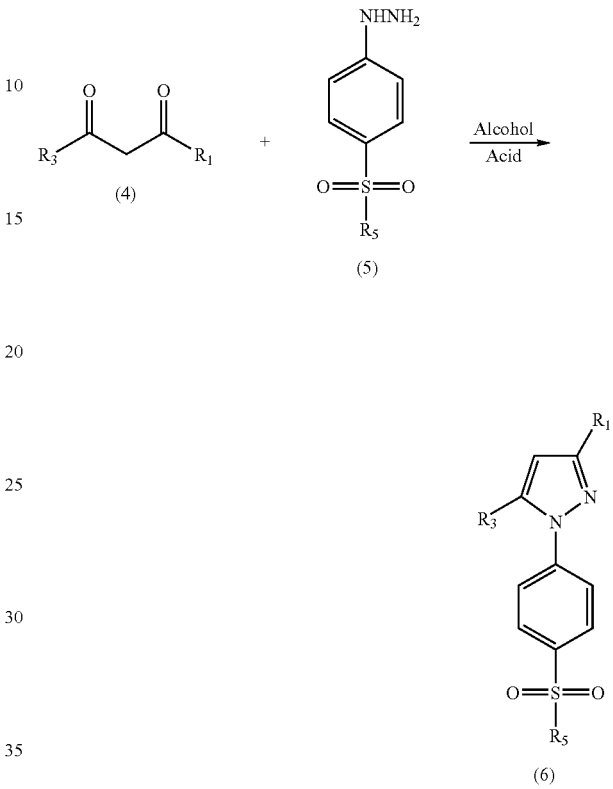

wherein $R_1$ and $R_3$ are as previously defined, and $R_5$ is methyl, amino (—$NH_2$), substituted amino or a salt thereof. Preferably in this embodiment, $R_1$ is trifluoromethyl, difluoromethyl, pentafluoroethyl or heptafluoropropyl, $R_3$ is phenyl optionally substituted at a substitutable position with one or more substituents selected from fluoro, chloro, bromo, methyl, ethyl, methoxy, methoxy, methylthio and hydroxyl, and $R_5$ is methyl, amino (—$NH_2$) or a salt thereof. In this embodiment, the acid is preferably a strong acid with a pKa of less than about 3.

In another embodiment, the substituents of the diketone (4) and hydrazine (5) are selected to yield celecoxib or the 4-fluorophenyl analog of celecoxib (4-[5-(4-fluorophenyl)-3-(trifluoromethyl)-1H-pyrazole-1-yl]benzenesulfonamide), sometimes hereinafter referred to as "celecoxib and celecoxib analog." In this embodiment, $R_1$ and $R_3$ of diketone (4) are —$CF_3$ and 4-methylphenyl or 4-fluorophenyl, respectively, and $R_5$ of hydrazine (5) is methyl or amino. As depicted in Reaction Scheme (III) below, diketone (7) (a sodium salt of 4-methylphenyl-1,1,1-trifluoro-2,4-butanedione) is condensed with a halide salt of 4-sulfamidophenyl hydrazine (8) ("4-SAPH•HX" wherein X is a halide) in an alcoholic solvent, preferably isopropanol, and in the presence of an acid, preferably trifluoroacetic acid ("TFA"), to form celecoxib.

Reaction Scheme (III):

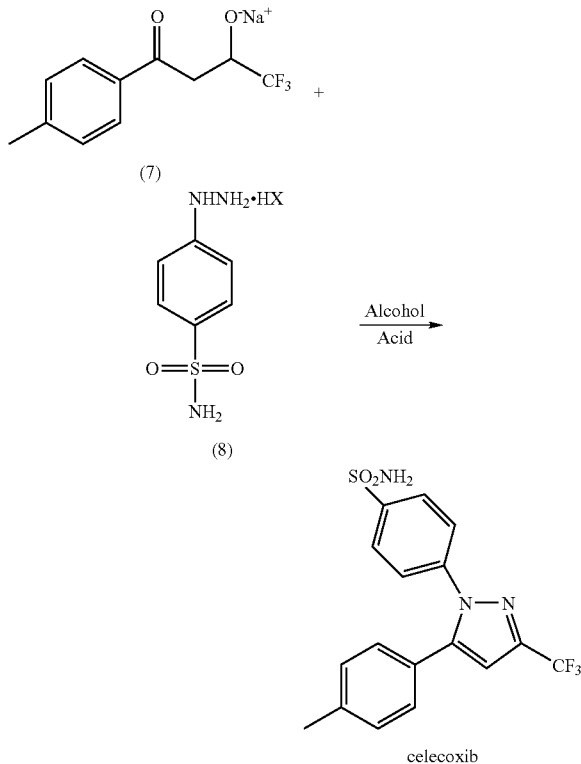

celecoxib

Diketone formation has been described in detail in Zhi, U.S. Pat. Nos. 5,892,053 and 5,910,597, both of which are incorporated herein by reference. In one embodiment, diketone (2) is prepared by treatment of a ketone (9) with an ester (10) and a base in a suitable solvent as depicted in Reaction Scheme (IV) below, and as described in detail in Zhi, U.S. Pat. Nos. 5,892,053 and 5,910,597.

Reaction Scheme (IV):

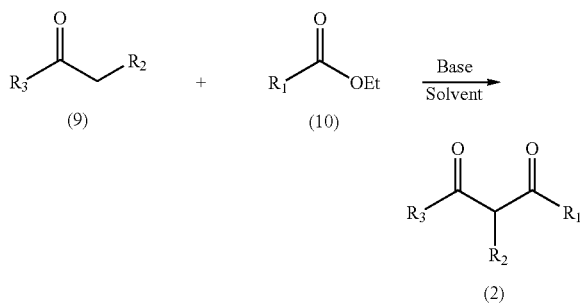

wherein $R_1$, $R_2$, and $R_3$ are as previously defined. In general, the base may be a base of sufficient strength to deprotonate ketone (9); preferably the base is sodium methoxide, potassium tert-butoxide or triethylamine. The solvent is typically an organic solvent or mixture of solvents which is/are inert under the reaction conditions. The solvent may be, for example, an aliphatic or aromatic hydrocarbon such as pentane, hexane, heptane, benzene, toluene or xylene, a cyclic or linear amide such as N-methyl-pyrrolidone, an ether such as THF or MTBE, or a lower alcohol such as trifluoroethanol, propanol or butanol.

In one embodiment, the diketone is prepared in an alcoholic solvent; for example lower secondary or tertiary alcohols such as isopropyl alcohol, isobutyl alcohol or tert-butyl alcohol may be used. For example, 4-methylacetophenone (4-MAP) or 4-fluoroacetophenone and ethyltrifluoroacetate (ETFA) may be reacted in the presence of a strong base in a solvent system comprised of an alcohol or mixed alcohols. As depicted Reaction Scheme (V), one equivalent of 4-MAP may be reacted with excess ETFA and sodium methoxide to generate the diketone sodium salt. Sodium methoxide solvated with methanol is generally preferred. An ETFA:4-MAP molar ratio of 1.01 to 1.5 is preferred, with a ratio of about 1.3 being especially preferred. A sodium methoxide:4-MAP molar ratio of 1.01 to about 1.5 is preferred, with a ratio of about 1.2 being especially preferred. The reaction is preferably conducted at a temperature less than the boiling point of the solvent system, and most preferably at about 50° C. The water content in the solvent system is preferably limited and may be, for example, less than about 0.1 w/w %. Isopropyl alcohol and tert-butyl alcohol are preferred solvents with isopropyl alcohol being most preerred.

Reaction Scheme (V):

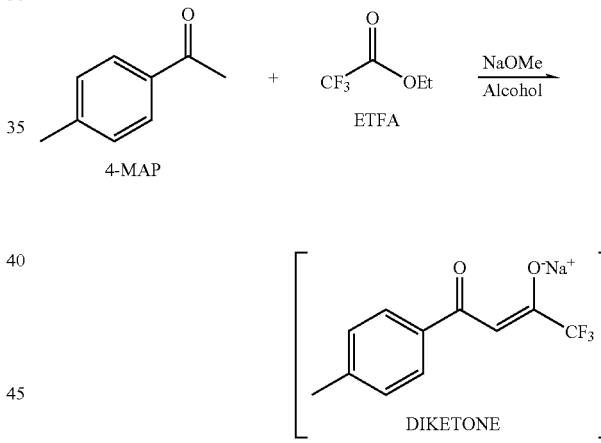

In the following description of the practice of the present invention, particular reference will be made to its application in the preparation celecoxib and the celecoxib analog. It should be recognized, however, that the principles disclosed herein are generally applicable to other pyrazoles and more particularly to 3-haloalkyl-1H-pyrazoles.

It has been discovered that by-product formation, for example regioisomer and hydroxyregioisomer, can be significantly reduced by minimizing diketone exposure to water before it is reacted with hydrazine in the 3-haloalkyl-1H-pyrazole formation reaction. Stated differently, the reactivity of diketone with water is believed to reduce selectivity for the formation of 3-haloalkyl-1H-pyrazole and increase by-product selectivity. Without being bound by any particular theory and based on evidence to date, it appears that the diketone can potentially exist in three different tautomeric species, designated below as A, B and C:

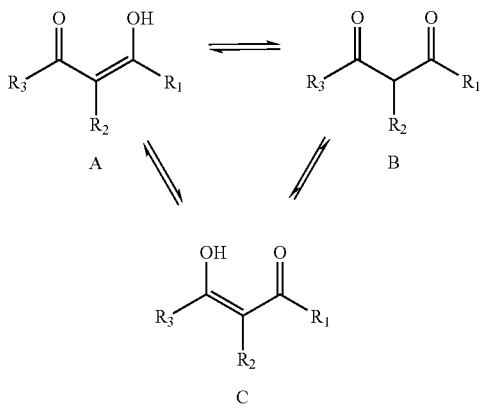

It further appears that water reacts with one of the carbons containing an oxygen group (carbonyl or hydroxyl) of the species A, B or C depicted above to form a diketone hydrate species. Moreover, it has been discovered that water will preferentially react with the ketone bearing the more electronegative group. For example, in the case where $R_2$ is hydrogen and $R_1$ is more electronegative than $R_3$, water will react almost exclusively at the carbon bearing the $R_1$ group to produce the hydrate species as depicted in the following reaction:

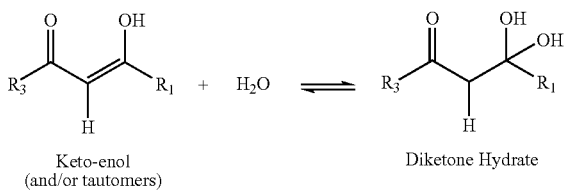

Keto-enol (and/or tautomers)    Diketone Hydrate

The hydrate then essentially acts as a blocking group against the reaction of hydrazine at the carbonyl center bearing the more electronegative group ($R_1$ in this example) which in turn allows a higher relative proportion of hydrazine to react at the more electropositive group ($R_3$) thereby adversely affecting the qualitative integrity of the prepared pyrazole.

In the case of celecoxib and the celecoxib analog, $R_1$ is $CF_3$, $R_2$ is hydrogen and $R_3$ is 4-methylphenyl or 4-fluorophenyl, with $CF_3$ being the most electronegative group. Hence, in the presence of water, a diketone hydrate preferentially forms at the carbon bearing the $CF_3$ group effectively blocking its availability as a hydrazine (4-sulfamidophenyl hydrazine, or "4-SAPH") reaction site. This allows a higher relative proportion of the 4-SAPH to react with the carbonyl center bearing the more electropositive (phenyl) group to form by-product. Exposure of the diketone to significant amounts of water for an appreciable period of time prior to the introduction of 4-SAPH to the reaction system tends to negatively impact the formation rate of celecoxib and the celecoxib analog and tends to lead to the formation of greater amounts of by-product. In general, therefore, minimizing the amount of water in the diketone reactant solution leads to increased selectivity for formation of celecoxib and the celecoxib analog thereby decreasing the amount of generated by-product and resulting in a high purity product.

In one embodiment, the molar equivalent ratio of water to diketone in the diketone source and in mixtures formed by combining the diketone source with the solvent system or other reaction mixture components before the diketone is combined with the 4-SAPH source is controlled to be less than about 50:1 water:diketone. For example, a water to diketone equivalent ratio of about 0.5 in the diketone source may be tolerated for a 25° C. isothermal addition of hydrazine to diketone added over a period of about 10 minutes. Depending upon the rate of addition, molar equivalent ratios of water to diketone of about 2, 5 and 10 may be acceptable for isothermal addition temperatures of 35° C., 45° C. and 55° C., respectively. In general, decreasing the rate of addition allows the system to tolerate greater water:diketone ratios. For example, at 45° C. molar equivalent ratios of water to diketone of about 10:1 and 50:1 may be acceptable in one embodiment provided the addition of hydrazine is carried out over a period of 20 and 60 minutes, respectively. Alternatively, hydrazine at room temperature may be added to diketone and water in an adiabatic manner with the reaction temperature rising from room temperature to about 50° C. to about 60° C. as a result of a combination of the diketone heat of neutralization and the heat of reaction. In this embodiment, a water:diketone equivalent ratio of about 2:1 may be acceptable. Under commercial operating conditions, therefore, the water to diketone molar equivalent ratio will typically be less than about 50:1, and more typically less than about 30:1.

Based upon evidence obtained to date, it appears that water and hydrazine competitively react with diketone, with reaction kinetics favoring pyrazole formation over diketone hydration. Hence, although the water content in the diketone source for the pyrazole formation reaction will typically be limited, the hydrazine source for this reaction may contain significant water concentrations. For example, in one embodiment in which a hydrazine source containing water is added to an alcoholic diketone source solution, greater proportions of water may be tolerated as the temperature of addition increases. For example, in one embodiment a water:diketone molar equivalent ratio of about 1000:1 may be tolerated for a 22° C. isothermal addition of hydrazine to diketone followed by heating to about 30° C. to about 70° C. for pyrazole formation. Alternatively, hydrazine at room temperature may be added to diketone and water in an adiabatic manner with the reaction temperature rising to about 30° C. to about 70° C. as a result of a combination of the diketone heat of neutralization and the heat of reaction.

In general, the ratio of by-product to celecoxib or the celecoxib analog appears to be related to the pKa of the acid used in the reaction mixture. Kinetic studies suggest that the rate of by-product formation decreases as the acid strength increases while the rate of formation of celecoxib and the celecoxib analog is relatively unaffected by acid strength. Based on those studies it is believed, without being bound to any particular theory, that the rate of by-product formation may be inversely proportional to the reactive system acid concentration while formation of celecoxib and the celecoxib analog may be independent of acid concentration. Hence, the relative ratio of the formation of celecoxib and the celecoxib analog to by-product generation, thus celecoxib and celecoxib analog purity, can be increased by using a strong acid. In one embodiment, therefore, the reaction mixture preferably comprises an acid having a pKa less than about 3, more preferably less than about 2, and still more preferably less than about 1. In this embodiment, preferred acids include TFA, hexafluorophosphoric, tetrafluoroborate, trichloroacetic, difluoroacetic, and dichloroacetic acids with TFA being especially preferred.

Based upon experimental evidence obtained to date, it appears the acid serves to maintain an acidic environment and solublize hydrazine in the reaction mixture, thereby making it available for reaction with diketone. It also appears the acid assures that the basic diketone solution is neutralized prior to reaction with hydrazine. Moreover, after the base has been neutralized in one embodiment it is preferred that the reaction system contain excess acid in order to provide a sufficient rate of hydrazine dissolution into the reaction mixture. Typically, the pH of the reaction mixture is maintained below about 2.5. Preferably, after base neutralization, the reaction mixture contains from about 0.1 to about 3 equivalents, more preferably about 0.1 to about 2 equivalents, and still more preferably about 0.1 to about 1 equivalent excess acid.

In general, 3-haloalkyl-1H-pyrazole and by-product formation rates tend to vary with hydrazine concentration relative to diketone concentration in solution in the reaction mixture. In the case of celecoxib and the celecoxib analog, it appears the reaction order in 4-SAPH is not the same for the formation of celecoxib versus the formation of hydroxyregioisomer. Without being bound to any theory and based on experimental evidence to date, the celecoxib and celecoxib analog formation reaction appear to be approximately first order for 4-SAPH concentration whereas the hydroxyregioisomer formation reaction appears to be at least second order for 4-SAPH concentration. Therefore, the ratio of rates between celecoxib and celecoxib analog formation versus formation of hydroxyregioisomer appear to be inversely proportional to the concentration of 4-SAPH in solution. This implies that a greater amount of by-product formation occurs with higher concentrations of 4-SAPH in solution, and by limiting that concentration celecoxib purity may be improved. In one embodiment, therefore, it is preferred that the solubilized molar equivalent ratio of hydrazine to diketone be maintained at a value less than about 2:1, more preferably less than about 1.5:1, and still more preferably less than about 1:1 during the pyrazole formation reaction. Although the total ratio of unsolubilized hydrazine:solubilized diketone may, and typically does exceed 2:1, in one embodiment the solubilized ratio is maintained within the preferred range for a significant percentage of the time allowed for pyrazole formation; for example, the solubilized ratio may exceed 2:1 during at least a portion of the reaction, most typically at the beginning or end of the reactant addition sequence where a stoichiometric excess of hydrazine may occur. In addition, in one embodiment, it is preferred that the concentration of hydrazine in solution in the reaction mixture be maintained at less than about 8 weight percent, and more preferably less than about 5 weight percent.

The temperature of the reaction mixture also tends to have an impact upon the relative formation of celecoxib and the celecoxib analog (or other pyrazole) versus by-product. At reaction temperatures exceeding about 22° C., reaction kinetics are favorable for pyrazole formation as compared to the competing diketone hydration and the hydroxyregioisomer formation reaction resulting from excess 4-SAPH in solution. Thus, reaction system tolerance for both water concentration and solubilized molar equivalent ratio of hydrazine to diketone increases as a function of reaction temperature. In one embodiment, therefore, the pyrazole formation reaction temperature is preferably between about 35° C. and about 70° C., more preferably between about 45° C. and about 65° C. and still more preferably between about 50° C. and about 60° C.

It further appears that the choice of solvent may have a qualitative impact on prepared 3-haloalkyl-1H-pyrazole. Generally, polar solvents lacking a group reactive with hydrazine such as alcohols, in combination with an acid of low pKa, have been found to preferably reduce by-product formation. In the formation of celecoxib a lower alcohol is preferred. Furthermore, lower alcohols containing at least three, e.g., three or four carbons were found to provide enhanced regioisomer selectivity over ethanol and methanol. Without being bound to any theory, it appears that the observed difference in by-product selectivity rests in the solvent's ability to form a diketone hemi-ketal species as a result of the reaction of the solvent with the carbonyl carbon bearing the most electronegative substituent. In the case of celecoxib, diketone hemi-ketal formation at the trifluoromethyl carbonyl may force hydrazine reaction at the other diketone carbonyl thus leading to increased by-product formation. Generally, lower alcohols containing one or two carbons more easily form a diketone hemi-ketal than do alcohols composed of three or four carbons. Preferred solvents are those that limit the formed pyrazole by-product levels to less than about 1% and include, for example, isopropyl alcohol, tert-butyl alcohol, and trifluoroethanol.

In addition to influencing the total amount of generated by-product, it has further been determined that solvents may influence the relative amounts of hydroxyregioisomer and regioisomer formed. Solvents which provide greater ratios are generally favored over those that either do not influence the ratio or decrease it because of the relative difficulty in separating regioisomer from celecoxib. In other words, reaction conditions that favor the formation hydroxyregioisomer as compared to regioisomer are preferred. It has been found that lower alcohols composed of three or four carbons provide preferred celecoxib to regioisomer ratios and may be used to generate celecoxib of high purity. In the formation of celecoxib, therefore, the solvent is preferably is isopropyl alcohol, tert-butyl alcohol, or trifluoroethanol, and most preferably isopropyl alcohol.

Many embodiments of the present invention are possible which take advantage of the various effects of the components and conditions described herein including, among others, the effect of water on by-product formation, the effect of hydrazine concentration on the rates of pyrazole and by-product formation, the effect of acid strength on the rates of pyrazole and by-product formation as well as acids preferred to qualitatively and quantitatively optimize prepared pyrazole and in particular celecoxib. Generally the various embodiments are directed to processes in which hydrazine concentration in solution in the reaction system is minimized and diketone exposure to water in the absence of hydrazine is also minimized.

In one embodiment, hydrazine concentration in the reaction system is preferably maintained low enough to disfavor by-product formation yet high enough to effectively compete with the diketone hydrolysis reaction and provide a commercially acceptable pyrazole preparation rate. Among the aspects of this invention, therefore, is to provide a reaction system that both minimizes 4-SAPH concentration in solution and the solubilized 4-SAPH:diketone molar ratio during the celecoxib formation reaction. Embodiments for accomplishing this objective include: (1) using a salt of 4-SAPH that has low solubility in the reaction solvent system, (2) slowly adding a soluble salt of 4-SAPH to the diketone, and (3) limiting the rate at which 4-SAPH is solubilized into the reaction solution.

In a first embodiment, a 4-SAPH salt exhibiting low solubility in the reaction solvent is added to an essentially non-aqueous diketone solution containing a metal salt of a strong acid with a pKa of less than about 3. Alcohols are the preferred solvent. In general, in this embodiment the 4-SAPH has a solubility in the organic solvent used for the pyrazole formation reaction of at least about 0.05 molar (at the temperature of reaction). As a result, 4-SAPH may be solubilized relatively rapidly upon salt exchange between the 4-SAPH salt and the strong acid salt. The 4-SAPH dissolution rate may be rapid enough to exceed the reaction rate with excess unreacted 4-SAPH in solution and elevated by-product levels resulting. This condition may occur in well-mixed reaction vessels wherein the reactants are present in essentially an ideal homogeneous mixture. The condition is exacerbated in reaction vessels that exhibit less than ideal mixing such as, for example: unbaffled reactors; where agitator speed, prop mixing characteristics, prop location relative to the reactor bottom, etc. have not been optimized to achieve adequate mixing; or a single-point 4-SAPH feed location. In such cases either generalized or localized excess 4-SAPH concentration may favor relatively large amounts of by-product formation. In this embodiment, therefore, the 4-SAPH addition rate is preferably controlled by means to minimize excess 4-SAPH in solution thereby maintaining the solubilized molar equivalent ratio of hydrazine to diketone less than about 2:1.

In a second embodiment, a soluble salt of 4-SAPH is added to diketone in an essentially non-aqueous solvent system. Alcohols are the preferred solvent. 4-SAPH salts with an alcohol solubility greater than about 0.05 molar are generally prepared from acids with a pKa of less than about 3. It has been found that 4-SAPH salts of mineral acids and some organic acids are generally not sufficiently soluble in alcohol for use in this embodiment. For example, in one embodiment the sulfuric, hydrochloric, phosphoric, nitric, p-toluenesulfonic and acetic acid salts of 4-SAPH have less than desired solubility in isopropyl alcohol. It has been found however that 4-SAPH salts of some strong acids have greater than about 0.05 molar solubility in alcoholic solvents. Preferred strong acids for use in this embodiment include hydrogen hexafluorophosphate, TFA, tetrafluoroborate, trichloroacetic, difluoroacetic, and dichloroacetic acids with TFA being especially preferred. In this embodiment, the high 4-SAPH salt solubility may result in either generalized or localized excess 4-SAPH concentration hence favoring a relatively large amount of by-product formation. The 4-SAPH salt addition rate is thus preferably controlled to assure that excess 4-SAPH is not present in solution, either in a localized or homogeneous excess concentration thereby maintaining the solubilized molar equivalent ratio of hydrazine to diketone less than about 2:1.

In a third embodiment, the 4-SAPH concentration in the reaction system is controlled by in situ conversion of 4-SAPH or a 4-SAPH halide salt, which have a solubility less than about 0.05 molar in the essentially non-aqueous solvent system, to 4-SAPH•Acid salt which is readily soluble in said solvent system. In a preferred approach for this embodiment, a halide salt of 4-SAPH (4-SAPH•HX) is converted in situ in the reaction system to 4-SAPH•HY using a strong base present in the alcoholic diketone solution and wherein $H^+Y^-$ is a strong acid with a pKa of less than about three (depicted below). Preferred acids for this purpose include TFA, hexafluorophosphoric, tetrafluoroborate, trichloroacetic, difluoroacetic, and dichloroacetic acids with TFA being especially preferred. The concentration of 4-SAPH in solution is a function of, and therefore may be controlled by, the amount of base added.

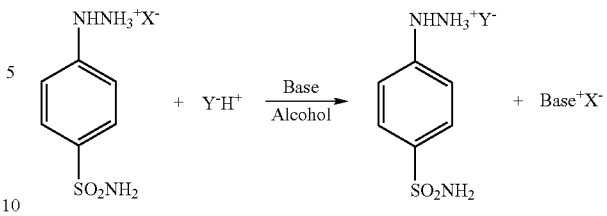

The process of the present invention may be used to develop commercially advantageous processes for the preparation of 3-haloalkyl-1H-pyrazoles, in general, in particularly high purity. For ease of discussion, however, and in view of the current commercial significance of celecoxib, certain of the various embodiments of the present invention have been described herein in the context of celecoxib and the celecoxib analog; it should be recognized, however, that these disclosures are generally applicable to other pyrazoles and more particularly to 3-haloalkyl-1H-pyrazoles.

In general, the present invention is directed to a process for the preparation of a crystallized reaction product constituting at least about 98% by weight of a 1-(4-sulfonylphenyl)pyrazole or a salt thereof by combining a source of a 1,3-diketone or a salt thereof with a source of 4-sulfonylphenylhydrazine or a salt thereof in a reaction mixture comprising a solvent system. In one embodiment, the water content of the 1,3-diketone source preferably contains less than about 50 equivalents, and preferably less than about 30 equivalents, and still more preferably less than about 10 equivalents of water per equivalent of 1,3-diketone. In another embodiment, when the 1,3-diketone is present as a salt, the water content of the 1,3 diketone source is preferably less than about 0.1 equivalents of water per equivalent of 1,3-diketone.

In one embodiment of the present invention, an alcoholic slurry of a 4-SAPH free base is added to a diketone solution containing a catalytic amount of a strong acid. In this embodiment, 4-SAPH is solubilized in situ upon addition to the diketone. The pyrazole formation reaction rate is generally faster than the rate of dissolution thereby maintaining the solubilized hydrazine:diketone molar ratio in the preferred range. In this way the reaction kinetics are favorable for formation of celecoxib and the celecoxib analog versus the competing by-product reaction. Metering techniques known in the art such as flow control, level control or cascaded flow control schemes driven by temperature control via a combination of heat of reaction and heat removal may be used to control the 4-SAPH addition rate.

If the strong acid is a mineral acid then the 4-SAPH may be either the free base or a mineral acid salt thereof and contain up to about 1000:1 equivalents of water per equivalent of 4-SAPH. In this case water is required for 4-SAPH dissolution in the diketone. Because water is introduced with 4-SAPH, rather than being present in the diketone, unacceptable levels of by-product tend to be avoided as the celecoxib and the celecoxib analog formation reaction kinetics are generally faster than the diketone hydration kinetics, thus preferentially favoring celecoxib and the celecoxib analog. If the strong acid is one providing 4-SAPH solubility in non-aqueous systems, such as for example TFA, water need not be present in the 4-SAPH source although a water to 4-SAPH equivalent ratio of up to about 1000:1 may be present in some embodiments.

A reverse order of addition may also be done wherein the diketone component is metered into the 4-SAPH component. In this scenario, the solubilized 4-SAPH:diketone ratio may exceed 2:1 if the diketone is added at an uncontrolled rate. In this embodiment, the diketone reactant is preferably metered into the 4-SAPH component at a controlled rate by means known in the art to maintain the solubilized 4-SAPH:diketone ratio in the preferred range.

In a second embodiment, an alcoholic slurry of a 4-SAPH salt with a solubility of less than about 0.05 molar in the reactive solvent system is added to a non-aqueous diketone solution containing the metal salt of acid that provides 4-SAPH solubility in non-aqueous solvents. In this embodiment 4-SAPH dissolution occurs as a salt-exchange reaction proceeds. For example, 4-SAPH may be present as a mineral acid salt, such as the HCl salt, that is of limited solubility in an alcoholic diketone solvent system, and the diketone solution may contain a metal salt of TFA or hydrogen hexafluorophosphate, such as sodium TFA. As 4-SAPH•HCl salt is added to the alcoholic diketone solution containing sodium TFA, the HCl salt is exchanged with TFA thus solubilizing the 4-SAPH. It is preferred to add the 4-SAPH component to the diketone at a controlled rate using methods known in the art to maintain the solubilized 4-SAPH:diketone molar ratio less than about 2:1 and disfavor by-product formation.

In a third embodiment, a 4-SAPH salt having a solubility in non-aqueous solvent systems greater than about 0.05 molar is added to a neutral diketone reaction system to prepare celecoxib or the celecoxib analog. In a first step of this embodiment the soluble 4-SAPH salt is prepared. Preferred salts include TFA, hexafluorophosphoric, tetrafluoroborate, trichloroacetic, difluoroacetic, and dichloroacetic acids with TFA being especially preferred. Reaction Scheme (VI) below depicts two preferred routes for the preparation of 4-SAPH•TFA.

In a second step of this embodiment, 4-SAPH•TFA is added to the diketone source to form celecoxib or the celecoxib analog. The 4-SAPH•TFA may be isolated and collected after its preparation. Alternatively and preferably, prepared 4-SAPH•TFA in solution may be combined with the diketone source to produce celecoxib or the celecoxib analog. In either case, however, the 4-SAPH•TFA is preferably metered into the diketone solution in a manner which minimize its concentration in the reaction mixture and thereby maintain the 4-SAPH:diketone solubilized molar ratio less than about 2:1. Liquid, solubilized 4-SAPH•TFA may be added by techniques known to those in the art as previously disclosed. Solid 4-SAPH•TFA may likewise be added by methods known to those in the art such as by solid feeders with rate controlled by weight added per unit time, or by other methods such as cascaded temperature control schemes as previously disclosed.

In one preferred embodiment for the preparation of celecoxib or the celecoxib analog, a metal salt of diketone in solution in a basic non-aqueous solvent solution is added to low solubility 4-SAPH•salt slurried in a non-aqueous solvent containing a strong acid that will form a 4-SAPH•salt with a solubility exceeding about 0.05 molar by salt exchange in the presence the base. Preferred low solubility 4-SAPH salts are formed from mineral acids, most preferably HCl. Preferred strong acids are hydrogen hexafluorophosphate, TFA, trichloroacetic, dichloroacetic and difluoroacetic, with TFA most preferred. The solvent is preferably an alcohol, most preferably isopropyl alcohol. In one preferred embodiment depicted in Reaction Scheme (VII) below, diketone sodium salt directly prepared by Reaction Scheme (V) or prepared by the reaction of the base sodium methoxide with diketone is added to 4-SAPH•HCl and TFA to form celecoxib.

Reaction Scheme (VI)

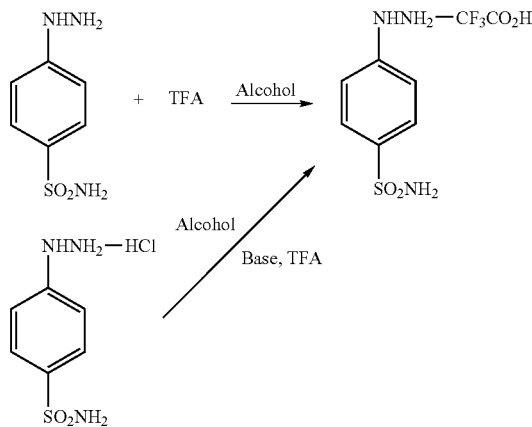

Reaction Scheme (VII):

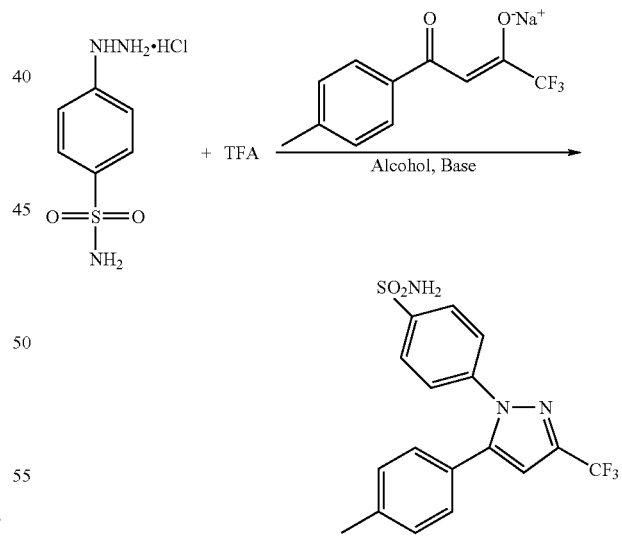

In the first route for 4-SAPH salt preparation (above), 4-SAPH free base is reacted with TFA in the presence of alcohol to form 4-SAPH•TFA. In a second route (above), 4-SAPH•HCl is reacted with a base and TFA in the presence of alcohol to form 4-SAPH•TFA. The base is preferably sodium methoxide or triethylamine and, in both routes, the alcohol is preferably isopropyl alcohol. In either route prepared 4-SAPH•TFA may be isolated and collected by methods known to those in the art such as, for example, solvent stripping to yield a slurry which may then be collected by solid-liquid separation techniques known in the art such as filtration or centrifugation.

In this scheme, the diketone sodium salt in solution in isopropyl alcohol, containing excess sodium methoxide base, is added to 4-SAPH•HCl that has been slurried in TFA-acidified isopropyl alcohol. As the diketone is added the sparingly soluble 4-SAPH•HCl is converted to readily soluble 4-SAPH•TFA in situ and solubilized into the isopropyl alcohol as the basic diketone is added. Advantageously, the rate of dissolution is generally less than the rate of reaction such that solubilized 4-SAPH is quickly consumed in the reaction with the diketone thereby maintaining the solubilized 4-SAPH:diketone ratio less than about 2:1. Thus, the 4-SAPH concentration in the reaction system is controlled at levels sufficiently low to selectively inhibit the by-product generation. The high reaction rate enables the diketone to be added at a rapid rate to the 4-SAPH•HCl slurry without associated elevated concentrations of 4-SAPH in solution. Hence diketone addition to the reaction system need not be controlled or metered, rather the addition rate is limited mainly by mass and heat transfer limitations. Thus the diketone is generally added to 4-SAPH•HCl at a rate limited only by maintenance of the moderately exothermic reaction system within the desired temperature range. Typically however, diketone addition rate is constrained more by transfer rate limitations than by high reaction temperature. The reaction is preferably carried out at a temperature of about 0° C. to about 70° C., more preferably about 10° C. to about 65° C. and most preferably about 20° C. to about 60° C.

Crude 3-haloalkyl-1H-pyrazole generated in the reaction of diketone and hydrazine typically requires further processing to achieve finished product purification requirements. The crude may be collected and purified generally by crystallization, isolation and solid washing techniques known by those in the art. Those techniques may involve volume reduction by continuous phase stripping to produce a concentrated high temperature solution followed by product crystallization via cooling. Alternatively, if the solubility curve is steep, the crude may simply be dissolved at concentration approaching saturation at an elevated temperature followed by crystallization by cooling. Generally, impurities preferentially remain in solution while the product crystallizes. The resulting solid product is then be collected by, for example, filtration or centrifugation whereby excess mother liquor with its contained impurities are removed. The collected intermediate may then be washed to further reduce contaminant levels and generate a purified product. Depending on final product specifications, the purified product may be further subjected to additional purification procedures.

Based on experimental evidence to date, it appears that the hydroxyregioisomer by-product will preferentially dehydrate to form the regioisomer by-product in strongly acidic aqueous systems. Hence, strongly acidic systems favor the regioisomer form. Disadvantageously, regioisomer is more difficult to separate from celecoxib than is hydroxyregioisomer as a larger portion of the regioisomer by-product crystallizes with the product from solution than does hydroxyregiosiomer. It has been discovered that addition of base to the reaction product mixture prior to the addition of water for celecoxib crystallization tends to inhibit hydroxyregioisomer dehydration. Of the total by-product formed in the condensation reaction, having at least a portion of the said by-product in the hydroxyregioisomer form increases the efficiency of the purification process and may yield celecoxib of the desired purity in one crystallization.

In one embodiment, therefore, the crystallization sequence involves first raising the reaction product mixture pH to a range of about 3 to about 9, typically about 5 to about 7, and more typically about 5.5 to about 6.5 with a base, preferably an aqueous sodium hydroxide solution of about 10% (w/w) to about 50% (w/w) concentration. The neutralized reaction product mixture is then heated to about 40° C. to about 80° C., more preferably about 50° C. to about 70° C., and most preferably about 55° C. to about 65° C. Water is added to the heated, neutralized reaction product while maintaining temperature, to a final concentration of about 15% (w/w) to about 35% (w/w) to dissolve substantially all of the salts in the reaction product mixture solid material.

A pH readjustment is then done with a base, preferably an aqueous sodium hydroxide solution of about 10% (w/w) to about 50% (w/w) concentration, to a pH of about 3 to about 9, more preferably about 5 to about 7, and most preferably from about 5.5 to about 6.5. While maintaining the temperature in the preferred range, water is added to a final concentration of about 25% (w/w) to about 50% (w/w), a concentration that corresponds to the preferred water:alcohol ratio of about 1:1 to about 1.5:1. Celecoxib is thereafter crystallized from solution by cooling the reaction product mixture to about 10° C. to about 30° C. over a period of about 1 hour to about 16 hours and isolated by any of a variety of solid-liquid separation techniques known to those skilled in the art including, but not limited to, centrifugation and filtration. The isolated celecoxib solid may then be further purified by washing with alcohol, preferably isopropyl alcohol of about 50% concentration in water, one or more times, and dried by any of a variety of techniques known to those skilled in the art including, but not limited to, fluidized bed drying, tray drying, filter-drying and blender-drying.

The overall process offers distinct advantages. First, the process of the present invention advantageously produces a celecoxib payload of at least 10% (w/w), more preferably 15% (w/w), and most preferably 20% (w/w). This result is enabled, in part, by the discovery that reacting kinetics disfavor by-product formation when the dissolved 4-SAPH concentration in the celecoxib formation reactive system is minimized. As a result, greater concentrations of diketone may be used while, at the same time, the dissolved 4-SAPH concentration may be limited, thus minimizing by-product formation. Advantageously, therefore, the process of the present invention may be practiced at a high payload while at the same time produce material of high purity.

Second, by limiting the exposure of diketone to water in the absence of hydrazine, diketone hydration may be minimized thereby minimizing by-product generation. Moreover, by limiting the ratio of solubilized hydrazine:diketone in the reactive system, reaction kinetics disfavor by-product formation and celecoxib of surprisingly high purity may be prepared.

Third, celecoxib purity requirements mandate removal of solvent. The use of an alcoholic solvent allows celecoxib crystallization without the formation of a solvate which advantageously results in both high process efficiency and payload. Also, because the efficiency of the present process is increased diketone need not be isolated; a crystallization step may be eliminated; solvent recovery and reuse is facilitated; and a single crystallization step reduces solvent use.

Another potential advantage is that reactor cleaning between production runs may be eliminated. In contrast, processes that utilize appreciable quantities of water during the celecoxib formation step require the remaining water to be purged from the reactor prior to diketone preparation and/or hydrazine introduction. Hence a reactor cleaning with associated health, safety, environmental, throughput and expense issues involved with exposure, release, disposal and specialized equipment and supplies is required. In one embodiment, the process of the present invention, by virtue of solvent unification for diketone and celecoxib preparation, and the preferred use of separate reaction vessels for substantially water-intolerant diketone and water-tolerant celecoxib enables reactor cleaning elimination that accrues the benefits of associated risk and cost avoidance, environmental burden reduction and commercial advantage through increased operational efficiency.

Fourth, the present process advantageously generates celecoxib of large particle size compared to certain other processes. In general, the process of the present invention may be used to generate celecoxib with an average particle size of about 40 µm to about 100 µm. Smaller particle crystals may tend to pack on solid-liquid separation equipment media such as filter or centrifuge screens and cloths, and reduce the space between crystals. The result is an increase in pressure drop across the media and an inhibition of liquid removal rate and efficiency. Similarly, small particle size material can impair drying processes through the tendency of the particles to adhere together and reduce available particle surface area for drying. Finally, small particles are easily pneumatically conveyed within the dryer and tend to migrate to and blind the dryer filter media, such as bags or screens. Pressure drop increases as the media blinds, and the dryer gas flow rate and associated drying efficiency decrease. Large particle size celecoxib attainable by the present process maximizes the efficiency of both solid-liquid separation and dryer operations thus enabling high payloads to be effectively processed.

Fifth, in the present process celecoxib may be crystallized from and washed with isopropanol:water mixed in a ratio of about 1:1. Because celecoxib solubility is reduced in the presence of water, more dissolution and loss of celecoxib in the isolated crystal mother liquor and wash liquor occurs in processes which utilize relatively lesser proportions of water. Additionally, the larger particle size crystals which may be derived from the process of the present invention usually present less surface area than do smaller crystals provided by other processes; thus dissolved material losses are reduced in the washing operation, and efficiency and payload are thereby increased.

Finally, the viscosity of the crystallized celecoxib slurry in the present process is greatly reduced, even at increased relative celecoxib concentration compared to other processes. In one embodiment of the present invention, the crystallized celecoxib slurry of the inventive process contains methanol (contained in the sodium methoxide base), increased water and decreased isopropanol concentrations, and is at a relatively high temperature; all of which contribute to reduced viscosity. Low viscosity enhances flow characteristics thus enabling accelerated flow rates, more efficient solid-liquid separation, and higher payload operation.

DEFINITIONS

Where the term "alkyl" is used, either alone or with another term such as "haloalkyl" and "alkylsulfonyl", it embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like.

The term "alkenyl" embraces linear or branched radicals having at least one carbon-carbon double bond of two to about twenty carbon atoms or, preferably, two to about twelve carbon atoms. More preferred alkyl radicals are "lower alkenyl" radicals having two to about six carbon atoms. Examples of such radicals include ethenyl, n-propenyl, butenyl, and the like.

The term "alkoxy" embraces linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The "alkoxy" radicals may be further substituted with one or more halogen atoms, such as fluoro, chloro or bromo, to provide "haloalkoxy" radicals. Examples of such radicals include fluoromethoxy, chloromethoxy, trifluoromethoxy, trifluoroethoxy, fluoroethoxy and fluoropropoxy.

The term "alkoxycarbonyl" means a radical containing an alkoxy radical, as defined above, attached via an oxygen atom to a carbonyl radical. Preferably, "lower alkoxycarbonyl" embraces alkoxy radicals having one to six carbon atoms. Examples of such "lower alkoxycarbonyl" ester radicals include substituted or unsubstituted methoxycarbonyl, ethoxycarbonyl, propoxycarbonyl, butoxycarbonyl and hexyloxycarbonyl.

The term "aminocarbonyl" denotes an amide group of the formula —C(=O)NH$_2$.

The terms "N-alkylamino" and "N,N-dialkylamino" denote amino groups which have been substituted with one alkyl radical and with two alkyl radicals, respectively. More preferred alkylamino radicals are "lower alkylamino" radicals having one or two alkyl radicals of one to six carbon atoms, attached to a nitrogen atom. Suitable "alkylamino" may be mono or dialkylamino such as N-methylamino, N-ethylamino, N,N-dimethylamino, N,N-diethylamino or the like.

The term "alkylthio" embraces radicals containing a linear or branched alkyl radical, or one to ten carbon atoms, attached to a divalent sulfur atom. An example of "alkylthio" is methylthio, (CH$_3$—S—).

The term "aryl", alone or in combination, means a carbocyclic aromatic system containing one, two or three rings wherein such rings may be attached together in a pendent manner or may be fused. The term aryl embraces aromatic radicals such as phenyl, naphthyl, tetrahydronaphthyl, indane and biphenyl.

The terms "carboxy" or "carboxyl", whether used alone or with other terms such as "carboxyalkyl" denotes —CO$_2$H.

The term "carbonyl" whether used alone or with other terms, such as "alkylcarbonyl" denotes —(C=O)—.

The term "cycloalkenyl" embraces unsaturated cyclic radicals having three to ten carbon atoms, such as cyclobutenyl, cyclopentenyl, cyclohexenyl and cycloheptenyl.

The term "cycloalkyl" embraces radicals having three to ten carbon atoms. More preferred cycloalkyl radicals are "lower cycloalkyl" radicals having three to seven carbon atoms. Examples include radicals such as cyclopropyl, cyclobutyl, cyclopentyl, cyclohexyl and cycloheptyl.

The term "electronegative" means the ability to become negatively charged through the acquisition of electrons. For example, halogens have high relative electronegativity. See, for example, Hawley, *The Condensed Chemical Dictionary*, Tenth Edition (1981) at page 406.

The term "ester" includes alkylated carboxylic acids or their equivalents, such as (RCO-imidazole).

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "heteroaryl" embraces unsaturated heterocyclic radicals. Examples of unsaturated heterocyclic radicals, also termed heteroaryl radicals, include unsaturated 5 to 6 membered heteromonocyclic group containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g., 1H-tetrazolyl, 2H-tetrazolyl, etc.], etc.; unsaturated condensed heterocyclic group containing 1 to 5 nitrogen atoms, for example, indolyl, isoindolyl, indolizinyl, benzotriazolyl, tetrazolopyridazinyl [e.g., tetrazolo [1,5-b] pyridazinyl, etc.], etc.; unsaturated 3 to 6-membered heteromonocyclic group containing an oxygen atom, for example, pyranyl, 2-furyl, 3-furyl, etc., unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g., benzoxazolyl, benzoxadiazolyl, etc.]; unsaturated 5 to 6-membered heteromonocyclic group containing 1 to 2 sulfur atoms and 1 to 3 nitrogen atoms, for example, thiazolyl, thiadiazolyl, [e.g., 1,2,4-thiadiazolyl, 1,3, 4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said "heterocyclic group" may have 1 to 3 substituents such as lower alkyl, hydroxy, oxo, amino and lower alkylamino. Preferred heterocyclic radicals include five to ten membered fused or unfused radicals. More preferred examples of heteroaryl radicals include benzofuryl, 2,3-dihydrobenzofuryl, benzothienyl, indolyl, dihydroindolyl, chromanyl, benzopyran, thiochromanyl, benzothiopyran, benzodioxolyl, pyridyl, thienyl, thiazolyl, oxazolyl, furyl, and pyrazinyl.

The term "heterocyclo" embraces saturated, partially saturated and unsaturated heteroatom-containing ring-shaped radicals, where the heteroatoms may be selected from nitrogen, sulfur and oxygen. Examples of saturated heterocyclic radicals include saturated 3 to 6-membered heteromonocyclic group containing 1 to 4 nitrogen atoms [e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclic radicals include dihydrothiophene, dihydropyran, dihydrofuran and dihydrothiazole.

The term "hydrogen" denotes a single hydrogen atom (H). This hydrogen radical may be attached, for example, to an oxygen atom to form a hydroxyl radical or two hydrogen radicals may be attached, for example, to an oxygen atom to form a hydroxyl radical or two hydrogen radicals may be attached to a carbon atom to form a methylene ($-CH_2-$) radical.

The term "hydrocarbyl" refers to radicals consisting exclusively of the elements carbon and hydrogen. These radicals include, for example, alkyl, cycloalkyl, alkenyl, cycloalkenyl, alkynyl, and aryl moieties. These radicals also include alkyl, cycloalkyl, alkenyl, cycloalkenyl, alkynyl, and aryl moieties substituted with other aliphatic or cyclic hydrocarbon groups, such as alkaryl, alkenaryl and alkynaryl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl.

The term "aminosulfonyl" denotes a sulfonyl radical substituted with an amine radical, forming a sulfonamide substituted with an amine radical, forming a sulfonamide ($-SO_2NH_2$).

The term "sulfonyl" whether used alone or linked to other terms such as alkylsulfonyl, denotes respectively divalent radicals $-SO_2-$. "Alkylsulfonyl" embraces alkyl radicals attached to a sulfonyl radical, where alkyl is defined as above. More preferred alkylsulfonyl radicals include methylsulfonyl, ethylsulfonyl and propylsulfonyl.

The following examples are simply intended to further illustrate and explain the present invention. This invention, therefore, should not be limited to any of the details in these examples.

Example 1

Comparison of Anhydrous vs. Added Water in the Celecoxib Synthesis Reaction

To a 100 mL Morton flask was charged 1 g 4-SAPH•HCl and 20 mL THF. To this slurry, under nitrogen at room temperature, was added 4.5 mL NaOH (1M in $H_2O$) to pH 11.2. The solution turned homogeneous. After 30 minutes the pH of the solution was adjusted to 0.9 with trifluoroacetic acid. At room temperature, 105 mg diketone, in 10 mL THF, was added. Aliquots were taken periodically as the reaction proceeded and analyzed by HPLC on a 4.6 mm, 5 micron Supelco Supelcosil® LC-DP column. HPLC analysis in all of the following examples was done by the same method. Results are given in table 1a below.

TABLE 1a

Celecoxib Synthesis With Added Water

| Time (min) | Percent Celecoxib | Percent Hydroxy regioisomer | Percent Regioisomer | Percent Diketone | Ratio of % Cele/ (% hydroxy + % regio) |
|---|---|---|---|---|---|
| 10 | 80.2 | 0.33 | 0.25 | 11.7 | 138.3 |
| 32 | 89.7 | 0.82 | 0.77 | 3.94 | 56.4 |
| 65 | 92.6 | 1.17 | 0.81 | 1.44 | 46.7 |
| 165 | 92.3 | 1.40 | 0.84 | 0.17 | 41.2 |
| 960 | 94.2 | 2.03 | 0.86 | N.D. | 37.6 |

To a 100 mL Morton flask was charged 1.03 g 4-SAPH and 20 mL THF. To this slurry, under nitrogen at room temperature, was added 1 g NaOMe (25 wt % in MeOH) to pH 10.4. The solution turned homogeneous. After 30 minutes the pH of the solution was adjusted to 1.1 with trifluoroacetic acid. At room temperature, 104 mg diketone, in 10 mL THF, was added. Aliquots were taken periodically as the reaction proceeded and analyzed by HPLC. Results are given in table 1b below.

TABLE 1b

Anhydrous Celecoxib Synthesis

| Time (min) | Percent Celecoxib | Percent Hydroxy regioisomer | Percent Regioisomer | Percent Diketone | Ratio of % Cele/ (% hydroxy + % regio) |
|---|---|---|---|---|---|
| 15 | 90.9 | 0.41 | 0.13 | 3.86 | 168.4 |
| 60 | 94.6 | 0.55 | 0.05 | 0.13 | 157.7 |
| 120 | 94.9 | 0.62 | 0.07 | N.D. | 137.5 |
| 960 | 96.0 | 0.64 | 0.06 | N.D. | 137.1 |

Example 2

Effect of Acid on Celecoxib Formation

A 50 mL 3-neck Morton flask was fitted with a thermometer, a reflux condenser and a nitrogen inlet. To this reactor was charged 25 mL isopropanol and 1 g (4.5 mmol) 4-SAPH-HCl, followed by the addition of 0.5 g triethylamine (4.4 mmol) to free base the 4-SAPH. The reaction mixture was allowed to stir for 15 minutes at room temperature. To the resultant slurry was added 0.87 g (9.2 mmol) chloroacetic acid. The mixture was allowed to stir at room temperature for 15 minutes. After this time period, 1 g (4.3 mmol) diketone was added and the reaction mixture was heated to 60° C. and held at this temperature for 2.5 hr. An aliquot was taken and analyzed via HPLC. The reaction was repeated with each of the following acids: acetic, dichloroacetic, trichoroacetic, and trifluoroacetic.

Comparative results are given in table 2 below.

TABLE 2

Effect of Acid on Celecoxib Formation

| Acid | pKa | Mole % celecoxib | Mole % OH-regioisomer | Celecoxib/OH-regiosomer |
|---|---|---|---|---|
| Trifluoroacetic | 0 | 99.4 | 0.6 | 164.2 |
| Trichloracetic | 0.65 | 99.3 | 0.7 | 141.3 |
| Dichloroacetic | 1.29 | 98.7 | 1.3 | 78.5 |
| Chloroacetic | 2.86 | 95.3 | 4.7 | 20.2 |
| Acetic | 4.76 | 64.1 | 35.9 | 1.79 |

Example 3

Celecoxib Reaction Solvent Studies

A 100 mL 3-neck Morton flask was fitted with a reflux condenser, a nitrogen inlet, a thermometer and a glass stopper. This setup was purged with nitrogen for 15 min after which time 1 g (4.47 mmol) 4-SAPH-HCl and 25 mL anhydrous methyl alcohol was charged to the flask. To the slurry was added 0.5 g (4.95 mmol) triethylamine at room temperature. After 15 minutes, 1 g (8.77 mmol) trifluoroacetic acid was added at room temperature. After 15 minutes at room temperature, the reaction mixture was heated to 55° C., 1 g solid diketone (4.3 mmol) was added all at once followed by 5 mL methyl alcohol to wash the addition funnel. Aliquots from the reaction mixture were taken and analyzed by HPLC. Results in mole % by-product formed based on celecoxib at reaction completion are show in table 3 below.

The reaction was repeated for the following solvents: Ethyl alcohol, n-Propyl alcohol, 1-Propyl alcohol, Trifluoroethanol, and t-Butyl alcohol.

TABLE 3

Celecoxib Reaction Solvent Studies

| Solvent | Mole % OH-Regioisomer | Mole % Regioisomer | Sum of By-Products |
|---|---|---|---|
| MeOH | 1.45 | 1.3 | 2.75 |
| EtOH | 1.47 | 0.37 | 1.84 |
| n-PrOH | 1.31 | 0.2 | 1.51 |
| i-PrOH | 0.75 | 0.09 | 0.84 |
| $CF_3CH_2OH$ | 0.05 | 0.59 | 0.64 |
| t-BuOH | 0.44 | 0.19 | 0.63 |

Example 4

Rate of Product Formation as a Function of Hydrazine Concentration

Into a 100 mL Morton flask fitted with a reflux condenser, a nitrogen inlet and a thermometer was weighed 67 mg 4-SAPH (free base, 0.36 mmol). To the 4-SAPH was added 15 mL isopropyl alcohol followed by 5 mL of a 0.36M TFA stock solution (in isopropyl alcohol). The mixture was heated to 40° C. with an oil bath giving a homogeneous solution. At 40° C. a 10 ml aliquot of a 0.036M 1,1,1-trifluoro-4-(4'-methylphenyl)-2,4-butanedione (in isopropyl alcohol) diketone stock solution, preheated to 40° C., was added all at once to the 4-SAPH mixture. Aliquots were taken periodically (200 μl), quenched in 0.2M NaOH (in 55:45 acetonitrile:water), and cooled in ice. Analysis was carried out by HPLC and area % values were converted to molar concentrations using standards. The results using four different concentrations of 4-SAPH are given in table 4 below for the initial rate of Celecoxib and Hydroxyregioisomer formation. The diketone concentration for all four trials was 12 mmolar.

TABLE 4

Initial Rate of Product Formation as a Function of Reagent Concentration

| [4-SAPH] (mmolar) | Rate OH-Regioisomer | Rate Celecoxib/ Rate HO-Regioisomer | [4-SAPH]:[diketone] |
|---|---|---|---|
| 6 | 0.00045 mmol/min | 174 | 1:0.5 |
| 12 | 0.0047 mmol/min | 88 | 1:1 |
| 18 | 0.015 mmol/min | 40 | 1.5:1 |
| 24 | 0.024 mmol/min | 35 | 2:1 |

Example 5

Concentration of 4-SAPH in Solution as a Function of Added Base

A 250 mL flask was charged with 11.3 g 4-SAPH•HCl (0.05 mol), 8.55 g TFA (0.075 mol) and 100.0 mL isopropanol to form a slurry. This was allowed to stir at room temperature for 30 min. To the 4-SAPH•HCl slurry was added NaOMe with 100 μL aliquots taken periodically. Each aliquot was diluted 1:10,000 with isopropyl alcohol and analyzed by UV-vis spectroscopy for 4-SAPH concentration. A summary of the results are given in Table 5a below. The procedure was repeated at 55° C. with the results reported in Table 5b below.

TABLE 5a

Concentration of 4-SAPH in Solution as a Function of Added Base (at Room Temperature)

| ml 25 wt % NaOMe added | mol NaOMe added | [NaOMe] molar | [4-SAPH] molar |
|---|---|---|---|
| 1 | 0.004 | 0.044 | 0.0176 |
| 2 | 0.009 | 0.088 | 0.0240 |
| 3 | 0.013 | 0.130 | 0.0464 |
| 4 | 0.018 | 0.172 | 0.0501 |
| 5 | 0.022 | 0.213 | 0.0650 |
| 7 | 0.031 | 0.292 | 0.0876 |
| 10 | 0.045 | 0.406 | 0.136 |
| 14 | 0.062 | 0.548 | 0.169 |

TABLE 5b

Concentration of 4-SAPH in Solution as a Function of Added Base (at 55° C.)

| ml 25 wt % NaOMe added | mol NaOMe added | [NaOMe] molar | [4-SAPH] molar |
|---|---|---|---|
| 0 | 0 | 0 | 0.0113 |
| 1 | 0.00446 | 0.0442 | 0.0308 |
| 2 | 0.00893 | 0.0875 | 0.0403 |
| 4 | 0.0179 | 0.172 | 0.0600 |
| 6 | 0.0268 | 0.253 | 0.087 |
| 10 | 0.0446 | 0.406 | 0.160 |
| 14 | 0.0625 | 0.548 | 0.184 |

Example 6

Conversion of Hydroxyregioisomer to Regioisomer Under Acidic Conditions

A 50 mL flask was charged with 200 mg hydroxyregioisomer of 89.8% purity as determined by HPLC. 25 mL of a 50/50 (v/v) solution of isopropyl alcohol and water were added. The pH was adjusted to 1.3 with hydrochloric acid. The reaction mixture was stirred at room temperature for 16 hours and then heated to 75° C. Aliquots from the reaction mixture were taken and analyzed by HPLC. Results in area % of hydroxyregioisomer and regioisomer are show in table 6 below.

TABLE 6

Conversion of hydroxyregioisomer to regioisomer under acidic conditions

| Temp (° C.) | Time (hr) | Percent Celecoxib | Percent OH-Regioisomer | Percent Regioisomer |
|---|---|---|---|---|
| Starting Material | 0 | 3.73 | 89.8 | 6.4 |
| Room Temp | 16 | 3.43 | 83.9 | 12.7 |
| 75 | 2 | 2.35 | 19.6 | 77.9 |
| 75 | 4 | 2.12 | 1.99 | 95.8 |

Example 7

Preparation of Celecoxib with Hydrazine Reactant Containing Water

To a 250 mL reactor which had been purged with nitrogen and which had been fitted with a mechanical stirrer and a chilled condenser was charged while stirring, isopropyl alcohol (50.75 g), ethyltrifluoroacetate (37.95 g), sodium methoxide (25% in methanol, 53.28 g) and 4'-methylacetophenone (27.43 g). The reaction mixture was heated to 50-55° C. and held for at least 2 hours. To a separate 1 L reactor which had been purged with nitrogen and fitted with a mechanical stirrer and a chilled condenser, was charged 4-SAPH•HCl (45.96 g), isopropyl alcohol (101.2 g), water (74 g) and trifluoroacetic acid (23.43 g). The 4-SAPH•HCl was heated to 50° C. with agitation. At the completion of the 2 hour reaction period, the contents of the first reactor was transferred to the second reactor containing the 4-SAPH•HCl over a period of at least five minutes and the reaction mixture was then brought to 55° C. and maintained at that temperature for at least 30 minutes. The pH of the reaction mixture was then adjusted to be within the range of 3 to 9 followed by the addition of water (95 g). The contents were then heated to 65° C. and the pH was again adjusted to be within the range of 3 to 9. Water (90 g) was then added to the mixture over a time period of about 20 minutes while maintaining the temperature at about 65° C. The reaction mixture was then cooled to about 20° C. over a period of 12 to 14 hours to produce celecoxib (62-65 g) with less than 0.05% regio-isomer and undetectable regioisomer.

Example 8

Preparation of Celecoxib with Anhydrous Hydrazine Reactant

To a 250 mL reactor which had been purged with nitrogen and which had been fitted with a mechanical stirrer and a chilled condenser was charged while stirring, isopropyl alcohol (50.75 g), ethyltrifluoroacetate (37.95 g), sodium methoxide (25% in methanol, 53.28 g) and 4'-methylacetophenone (27.43 g). The reaction mixture was heated to 50-55° C. and held for at least 2 hours. To a separate 1 L reactor which had been purged with nitrogen and fitted with a mechanical stirrer and a chilled condenser, was charged 4-SAPH•HCl (45.96 g), isopropyl alcohol (101.2 g) and trifluoroacetic acid (23.43 g). The 4-SAPH•HCl was heated to 50° C. with agitation. At the completion of the 2 hour reaction period, the contents of the first reactor was transferred to the second reactor containing the 4-SAPH•HCl over a period of at least five minutes and the reaction mixture was then brought to 55° C. and maintained at that temperature for at least 30 minutes. The pH of the reaction mixture was then adjusted to be within the range of 3 to 9 followed by the addition of water (95 g). The contents were then heated to 65° C. and the pH was again adjusted to be within the range of 3 to 9. Water (90 g) was then added to the mixture over a time period of about 20 minutes while maintaining the temperature at about 65° C. The reaction mixture was then cooled to about 20° C. over a period of 12 to 14 hours to produce celecoxib (62-65 g) with less than 0.05% regio-isomer. Analysis of the reaction mixture prior to initiation of crystallization indicated that the regio-isomer content was less than 0.5 mole percent of the reaction products.

Example 9

Preparation of Celecoxib by Addition of Diketone Salt to 4-SAPH-HCl

To a 250 mL reactor, fitted with a mechanical stirrer and maintained under a nitrogen atmosphere, was added isopropyl alcohol (54.8 g, 0.912 moles), ethyl trifluoroacetate (38.0 g, 0.267 moles) and 25% sodium methoxide in methanol (53.3 g, 0.246 moles). To the agitated reactor was added 4-methylacetophenone (27.6 g, 0.206 moles). The reaction mixture was heated to 50° C. and maintained for 2 hours. To a second (1 liter) reactor was added 4-sulphamidophenyl hydrazine hydrochloride (46.0 g, 0.206 moles), isopropyl alcohol (101.3 g, 1.685 moles) and trifluoroacetic acid (11.7 g, 0.103 moles) with stirring. The reaction mixture was heated to approximately 45° C. Upon completion of the 2-hour reaction period in the 250 mL reactor, the contents was added to the second reactor over approximately 10 minutes. The reaction mixture maintained at 55° C. for 30 minutes. The pH was adjusted with 50% aqueous sodium hydroxide to a pH of 5-6. The reaction mixture was heated to 65° C. and water was added (95 g, 5.3 moles). The pH was again adjusted with 50% aqueous sodium hydroxide to a value of 5-6. Water (90 g, 5.0 moles) was added over 20 minutes while maintaining the temperature at 65° C. The reaction mixture was then cooled over 9 hours to 20° C. The reaction mixture was filtered, washed twice with 50% aqueous isopropyl alcohol and dried in a vacuum over for 16 hours to yield celecoxib (65.6 g) whose HPLC retention time was identical to that of authentic celecoxib. Regio-isomer was not detected by HPLC.

Example 10

Preparation of Celecoxib by the Addition of 4-SAPH-HCl to Diketone

To a 1 L reactor fitted with a mechanical stirrer and maintained under a nitrogen atmosphere, was added isopropyl alcohol (54.7 g, 0.912 moles), ethyl trifluoroacetate (37.7 g, 0.267 moles), and 25% sodium methoxide in methanol (53.3 g, 0.247 moles). To the agitated reactor was added 4-methylacetophenone (27.32 g, 0.205 moles). The reaction mixture was heated to 50° C. and maintained for 2 hours. Trifluoroacetic acid (36.69, 0.321 moles) was added to the reaction mixture over a period of five minutes. 4-SAPH-HCl (46.0 g, 0.205 moles) was added through a power addition funnel over a period of 10 minutes. The reaction mixture was brought to 55° C. and maintained for one hour. Isopropyl alcohol (81.5 g, 1.36 moles) was added followed by the addition of 50% sodium hydroxide (18.5 g, 0.231 moles) to achieve a pH of 7. Water (87.8 g, 4.88 moles) was added and the reaction mixture heated to 65° C. Water (90.0 g 5.00 moles) was added over ten minutes. The reaction mixture was cooled to 20° C. over nine hours. The slurry was filtered and washed twice with 50% (weight) aqueous isopropyl alcohol (100 g). The solid was dried in a vacuum oven for 16 hours to yield celecoxib (67.2 g) whose HPLC retention time was identical to that of authentic material. Regio-isomer was not detected by HPLC.

Example 11

Preparation of 4-[5-(4-Fluorophenyl)-3-trifluoromethyl-1H-pyrazol-1-yl]benzenesulfonamide To a 500 mL reactor fitted with a mechanical stirrer and maintained under a nitrogen atmosphere, was added isopropyl alcohol (29.3 g, 0.516 moles), ethyltrifluoroacetate (27.2 g, 0.191 moles) and 25% sodium methoxide in methanol (37.5 g, 0.173 moles). To the agitated reactor was added 4-fluoroacetophenone (20.0 g, 0.144 moles). The reaction mixture was heated to 55° C. and maintained for 2.25 hours. To a second (1 liter) reactor was added 4-sulfamidophenyl hydrazine chloride (46.0 g, 0.144 moles), isopropyl alcohol (96.6 g, 1.61 moles) and trifluoroacetic acid (8.25 g, 0.072 moles) with stirring. The reaction mixture was maintained at 50-55° C. for 30 minutes. The reaction mixture was cooled to 33° C. over 2.5 hours and then to 20° C. over 8 hours. The pH was adjusted with 50% sodium hydroxide to a pH of 6 to 7. The reaction mixture was filtered and washed with 1/1 (v/v) IPA/water (104 g). The remaining solid was dried to yield 4-[5-(4-Fluorophenyl)-3-trifluoromethyl-1H-pyrazol-1-yl] benzenesulfonamide (41.6 g) whose HPLC retention time was identical to that of standard material. No regio-isomer was detected by HPLC.

What is claimed is:

1. A process for the preparation of (4-[5-(4-methylphenyl)-3-(trifluoromethyl)-1H-pyrazole-1-yl]benzenesulfonamide) or (4-[5-(4-fluorophenyl)-3-(trifluorornethyl)-1H-pyrazole-1-yl]benzenesulfonamide), the process comprising reacting a 1,3-diketone and a 4-sulfamidophenyl hydrazine halide salt in a reaction mixture comprising a solvent system containing an alcohol wherein said alcohol is selected from isopropanol, trifluoroethanol and t-butanol, wherein the solvent system comprises less than 30 equivalents of water per equivalent of 1,3-diketone, the 1,3-diketone being a metal salt of 4-methylphenyl-1,1,1-trifluoro-2,4-butanedione or a metal salt of 4-fluorophenyl-1,1,1-trifluoro-2,4-butanedione, the reaction mixture being formed by combining a source of the 3-diketone, a source of the 4-sulfamidophenyl hydrazine halide salt, and the solvent system, said 1,3-diketone source additionally comprising a base and the 4-sulfamidophenyl hydrazine halide salt source additionally comprising trifluoroacetic acid and crystallizing a solid reaction product containing the (4-[5-(4-methylphenyl)-3-(trifluoromethyl)-1H-pyrazole-1-yl]benzenesulfonamide) or (4-[5-(4-fluorophenyl)-3-(trifluoromethyl)-1H-pyrazole-1-yl] benzenesulfonamide) from the reaction mixture, the (4-[5-(4-methylphenyl)-3-(trifluoromethyl)-1H-pyrazole-1-yl]benzenesulfonamide) or (4-[5-(4-fluorophenyl)-3-(trifluoromethyl)-1H-pyrazole-1-yl] benzenesulfonamide) constituting at east about 98% by weight of the solid reaction product.

2. The process of claim 1 wherein the 4-sulfamidophenyl hydrazine halide salt is the hydrochloride salt and the metal salt of 4-methylphenyl-1,1,1-trifluoro-2,4-butanedione or 4-fluorophenyl-1,1,1-trifluoro-2,4-butanedione is the sodium salt.

3. The process of claim 1 wherein the base is sodium methoxide and the solvent system comprises isopropyl alcohol.

4. The process of claim 1 wherein the 1,3-diketone source is added to the 4-sulfamidophenyl hydrazine source.

* * * * *